United States Patent

Bröcker et al.

[11] Patent Number: 6,162,758
[45] Date of Patent: Dec. 19, 2000

[54] PROCESS FOR DEHYDROGENATING SECONDARY CYCLIC ALCOHOLS

[75] Inventors: Franz Josef Bröcker, Ludwigshafen; Michael Hesse, Worms; Robert Märkl, Fussgönheim, all of Germany

[73] Assignee: BASF Aktiengesellschaft, Ludwigshafen, Germany

[21] Appl. No.: 09/142,218

[22] PCT Filed: Mar. 6, 1997

[86] PCT No.: PCT/EP97/01124

§ 371 Date: Sep. 3, 1998

§ 102(e) Date: Sep. 3, 1998

[87] PCT Pub. No.: WO97/33853

PCT Pub. Date: Sep. 18, 1997

[30] Foreign Application Priority Data

Mar. 14, 1996 [DE] Germany .......................... 196 09 954

[51] Int. Cl.⁷ .............................. B01J 23/02; C07C 45/65
[52] U.S. Cl. ......................... 502/340; 502/307; 568/338; 568/361; 568/366; 585/379
[58] Field of Search ............................ 585/379; 502/307, 502/340; 568/338, 361, 366

[56] References Cited

U.S. PATENT DOCUMENTS 3,305,587  2/1967  Sperbert et al. ........................ 260/586
3,350,456  10/1967  Fueg ........................................ 260/586
3,875,239  4/1975  Stouthamer et al. .................... 260/596
3,981,923  9/1976  Stouthamer et al. .................... 260/596

FOREIGN PATENT DOCUMENTS 1 296 625  6/1969  Germany .
1 443 462  8/1969  Germany .
2 028 350  12/1970  Germany .
1 054 617  1/1967  United Kingdom .

OTHER PUBLICATIONS

Chem. Abstracts, vol 121, 1994.

Chem. Abstracts, vol 111, No. 14, 1989.

Acta. Chim. Acad. Sci. Hung, 97, 1978, pp. 439–449.

Acta. Chim. Acad. Sci. Hung, 107, pp. 343–360 (1981).

*Primary Examiner*—Sreeni Padmanabhan
*Attorney, Agent, or Firm*—Keil & Weinkauf

[57] ABSTRACT

In the dehydrogenation of secondary alcohols in the presence of a catalyst comprising zinc oxide and calcium carbonate at elevated temperature in the gas phase, secondary cyclic alcohols are used and the dehydrogenation is carried out in the presence of hydrogen and a catalyst whose active components comprise from 30 to 60% by weight of zinc oxide and from 40 to 70% by weight of calcium carbonate in the calcite modification.

11 Claims, No Drawings

PROCESS FOR DEHYDROGENATING SECONDARY CYCLIC ALCOHOLS

This is the U.S. National stage application of PCT/EP97/01124 filed Mar. 6, 1997.

The present invention relates to a process for dehydrogenating secondary alcohols in the presence of a catalyst comprising zinc oxide and calcium carbonate at elevated temperature in the gas phase.

DE-A 1,443,462 discloses a process for dehydrogenating primary and secondary alcohols in which the alcohol used is dehydrogenated at elevated temperature in the gas phase over catalysts consisting predominantly of zinc oxide to give the corresponding aldehyde or ketone. The catalyst can contain both copper compounds and alkaline earth metals. During the dehydrogenation, ie. after hydrogen elimination has commenced, the hydrogen feed in the process described is discontinued. In particular, the dehydrogenation of cyclohexanol to cyclohexanone is described, but the yield of cyclohexanone is only 81.5%. Apart from 17% of unreacted cyclohexanol, the reaction mixture contains from 0.1 to 0.5% of hydrocarbons and 1% of higher-boiling condensation products.

DE-B 1,296,625 describes a process for preparing cyclohexanone from cyclohexanol contaminated with organic acids and esters at elevated temperatures in the presence of a zinc-containing catalyst comprising zinc oxide-zinc carbonate or mixtures of zinc oxide-zinc carbonate with calcium oxide-calcium carbonate or with magnesium oxide-magnesium carbonate. A disadvantage of this process is the excessive decrease in the pellet hardness in long-term operation which leads to frequent replacement of the catalyst and corresponding down times. The decrease in the pellet hardness in long-term operation results from the massive decomposition of the carbonates by organic acids or from phase transformations.

Acta Chim. Acad. Sci. Hung 107 (1981) 343–360, Acta Chim. Acad. Sci. Hung 97 (1978) 439–449 disclose that in the dehydrogenation of cyclohexanol in the presence of hydrogen and catalysts comprising elements of the eighth transition group, e.g. rhodium, nickel and platinum, increased amounts of cracking products and formation of phenol and benzene are observed in comparison with processes not using hydrogen. This is not observed in the dehydrogenation of aliphatic alcohols: thus DE-A 2,028,350 describes a process for dehydrogenating aldehydes and ketones, in particular for preparing acetone and methyl isobutyl ketone, over a copper-containing catalyst in the presence of hydrogen. It may be remarked that although this reference mentions cyclohexanol as starting material among many others, there are no experimental data on the dehydrogenation of cyclohexanol. In all probability it would also be possible to prepare cyclohexanone by the process described in DE-A 2,028,350, but in the light of the above-mentioned Acta Chim. Acad. Sci. Hung 107 (1981) 343–360 and also Acta Chim. Acad. Sci. Hung 97 (1978) 439–449 one would have to expect by-products which prohibit economical use.

It is an object of the present invention to provide a process in which cyclic ketones, in particular cyclohexanone, can be obtained in higher selectivities and yields than hitherto possible and in which the formation of cracking products and aromatic by-products is minimized. The present invention is also to make available a catalyst which in long-term operation has a good pellet hardness, particularly in respect of compressive strength on the end face and lateral compressive strength, so that the catalyst has to be replaced less often than hitherto.

We have found that this object is achieved by a process for dehydrogenating secondary alcohols in the presence of a catalyst comprising zinc oxide and calcium carbonate at elevated temperature in the gas phase, wherein secondary cyclic alcohols are used and the dehydrogenation is carried out in the presence of hydrogen and a catalyst whose active components comprise from 30 to 60% by weight of zinc oxide and from 40 to 70% by weight of calcium carbonate in the calcite form.

In addition, a dehydrogenation catalyst and a process for its preparation and its use have been found.

Secondary alcohols which can be used according to the present invention are cycloaliphatic alcohols having from 5 to 16 carbon atoms, for example cyclopentanol, cyclohexanol, 4-methylcyclohexanol, cyclooctanol, cyclododecanol and cyclohexadecanol, preferably cyclohexanol.

The zinc oxide-containing catalyst used according to the present invention is a catalyst whose active components comprise from 30 to 60% by weight, preferably from 40 to 50% by weight, of zinc oxide and from 40 to 70% by weight, preferably from 50 to 60% by weight, of calcium carbonate in the calcite form.

In a preferred embodiment, the catalyst of the present invention has a BET specific surface area of from 5 to 50 $m^2/g$, preferably from 10 to 30 $m^2/g$.

Such a catalyst is obtainable according to the present invention by precipitation of sparingly soluble zinc and calcium compounds from water-soluble zinc and calcium compounds using a base and subsequent work-up in a manner known per se, wherein (a) the base used is a water-soluble basic carbonate, (b) if desired, the sparingly soluble zinc and calcium compounds are filtered off after precipitation, (c) the zinc and calcium compounds, which may have been filtered off, are washed, (d) the washed zinc and calcium compounds from (c) are dried to give a powder, and subsequently (e) the powder from (d) is calcined at not above 600° C., and (f) if desired, the calcined powder is pressed to give shaped bodies.

Water-soluble zinc and calcium salts which can be used are acetates, sulfates, nitrates, preferably nitrates such as zinc nitrate, zinc acetate, zinc sulfate, calcium acetate, calcium nitrate, preferably zinc nitrate and calcium nitrate. The aqueous solutions of the appropriate salts usually have concentrations in the range from 3 to 25% by weight, preferably from 10 to 25% by weight, in particular 20% by weight.

The molar ratio of zinc to calcium is selected such that after calcination the active components of the catalyst comprise from 30 to 60% by weight of zinc oxide and from 40 to 70% by weight of calcium carbonate in the calcite form.

Bases used are water-soluble basic carbonates such as alkali metal carbonates, e.g. sodium carbonate, potassium carbonate, alkali metal hydrogen carbonates, e.g. sodium hydrogen carbonate, potassium hydrogen carbonate, ammonium carbonate or ammonium hydrogen carbonate and mixtures thereof, preferably sodium carbonate, particularly preferably in the form of its aqueous solutions generally having concentrations in the range from 0.5 to 30, preferably from 10 to 25, gram of base/100 gram of solution.

The precipitation is generally carried out at from 10 to 900° C., preferably from 40 to 80° C. After the precipitation, the precipitate can be filtered off if desired. The precipitate, which may have been filtered off, is generally washed with water, preferably until nitrate can no longer be detected by means of the nitrate ring test, and is subsequently dried at preferably from 90 to 150° C. to give a dry powder. Drying can be carried out in a static or moving bed, preferably by spray drying.

According to the present invention, the dried powder is calcined at not above 600° C., preferably in the range from 300 to 600° C., in particular from 400 to 475° C., preferably in air. According to observations up to now, prolonged heating at above 600° C. leads to the formation of the aragonite form of $CaCO_3$. Brief heating to above 600° C. is not detrimental to the preparation of the catalysts of the present invention, as long as no aragonite is formed (ie. cannot be detected by means of X-ray diffractometry).

After calcination, the calcined powder can, if desired, be pressed to give shaped bodies such as pellets, rings, cylinders, etc., preferably pellets.

In a preferred embodiment, the calcined powder is pressed together with graphite, preferably with from 0.1 to 5% by weight, particularly preferably from 1 to 2.5% by weight, in particular 2% by weight, of graphite, based on the total mass.

In a further preferred embodiment, the uncalcined powder from step (c) (see above) is pressed to form shaped bodies, preferably to form pellets, and the shaped bodies thus obtained are calcined as described under step (d).

The calcined powders and shaped bodies thus obtained can be used as catalysts, these catalysts containing zinc oxide and calcium carbonate (in the calcite form) as active components and, if desired, graphite as passive component.

The catalysts of the present invention have the following physical properties:

In a further preferred embodiment, the catalyst of the type claimed in the present invention has a pore volume in the range from 0.10 to 0.50 $cm^3/g$, in particular from 0.20 to 0.35 $cm^3/g$, at a pore diameter in the range from 5 nm to 300 $\mu$m, where particularly preferably at least 85%, preferably more than 90%, of this pore volume is associated with a pore diameter in the range from 0.01 to 0.5 $\mu$m.

Particularly preferred catalysts of the type mentioned are those which have a compressive strength on the end face in the range from 500 to 4000 $N/cm^2$, in particular from 1000 to 2500 $N/cm^2$ and a lateral compressive strength of from 30 to 300 N, preferably from 50 to 200 N. These values can also be achieved without calcination. The important thing is that these strength ranges are retained under operating conditions (reaction conditions). However, this is only the case if no phase transformations occur. This condition is met by the process of the present invention.

The BET specific surface area is generally from 5 to 50 $m^2/g$, preferably from 10 to 30 $m^2/g$. The pore volume in the pore diameter range from 5 nm to 300 $\mu$m is usually from 0.1 to 0.5 $cm^3/g$, preferably from 0.2 to 0.35 $cm^3/g$, with the proviso that at least 85%, preferably more than 90%, of this pore volume is in the pore diameter range from 0.01 to 0.5 $\mu$m.

The compressive strength on the end face of the pellets is preferably from 500 to 4000 $N/cm^2$, in particular from 1000 to 2500 $N/cm^2$ and the lateral compressive strength of the pellets is preferably from 30 to 300 N, preferably from 50 to 200 N.

In a particularly preferred embodiment, the precipitate of sparingly soluble zinc and calcium compounds, preferably zinc hydroxide carbonate and calcium carbonate, is washed on filter presses, the filter cake thus obtained is slurried with water and the slurry is dried by spraying in a spray dryer.

The spray-dried powder obtained in this way can then be further processed as described above.

According to the present invention, the gaseous secondary, cyclic alcohol, preferably cyclohexanol, into which from 1 to 20% by volume, preferably from 5 to 10% by volume, of hydrogen, based on the amount of alcohol, has been mixed is brought into contact with the catalyst used in a manner customary per se, for example in a fixed-bed reactor or in a fluidized-bed reactor, preferably in a tube reactor in which the catalyst is arranged as a fixed bed. The product mixture is usually worked up by distillation.

In general, the alcohol to be used is vaporized in a manner known per se, for example in a vaporizer, and the desired amount of gaseous hydrogen is then mixed in.

The temperature of the gas phase in the reaction zone is usually selected so as to be in the range from 200 to 500° C., preferably from 300 to 450° C. In a preferred embodiment, the temperature range is selected such that a conversion in the range from 50 to 90%, preferably from 65 to 75%, of alcohol is obtained. In the case of cyclohexanol as starting compound, the temperature is selected so as to be in the range from 350 to 400° C.

The pressure of the gas phase in the reaction zone is generally selected so as to be in the range from 80 to 4000 kPa, preferably from 100 to 1000 kPa.

The space velocity over the catalyst is generally selected so as to be in the range from 0.5 to 3.0, preferably from 0.6 to 2.0, liters of alcohol per liter of catalyst per hour.

In a preferred embodiment, the hydrogen is separated from the reaction mixture leaving the reaction zone and is added to the gas mixture entering the reaction zone.

The ketones such as cyclohexanone prepared according to the present invention are important large-scale industrial products. For example, cyclohexanone is customarily further used, preferably in the resulting mixture with cyclohexanol, for preparing adipic acid.

The advantage of the process of the present invention is that cyclic ketones, in particular cyclohexanone, can be obtained in higher yields than hitherto possible, and the formation of cracking products and aromatic by-products is minimized.

EXAMPLES

Example 1

Preparation of a Calcined Catalyst ($Cl_0$)

For the preparation of the catalyst, two solutions are required. Solution 1 is an aqueous solution of zinc nitrate and calcium nitrate having a concentration of 20% by weight in which the molar ratio of zinc:calcium =1:1.6. Solution 2 is a 2M aqueous sodium carbonate solution.

Both solutions are heated to 70° C. and pumped in parallel into a precipitation vessel. The feed rate of the solutions is regulated such that a pH of 7.8±1.0 is maintained during the precipitation. The precipitate obtained in this parallel precipitation is filtered off and washed with water until nitrate can no longer be detected (test using $FeSO_4$ solution and concentrated $H_2SO_4$, known as the nitrate ring test). The precipitate is subsequently slurried in water and spray dried. The powder thus obtained is heated in air for 5 hours at 450° C. and, after cooling and addition of 2% by weight of graphite, pressed to give 5×5 mm pellets. The physical data for the catalyst ("$Cl_0$") are shown in Table 1.

Example 2

Dehydrogenation Using $Cl_0$ 920 g of the catalyst $Cl_0$ prepared as described in Example 1 were installed in a tube reactor having a length of 0.6 m and an internal diameter of 0.05 m. Via a vaporizer, 640 ml/h of liquid cyclohexanol were fed in gaseous form into the reactor. 7 l/h of hydrogen were metered in upstream of the reactor. The temperature of the reaction mixture in the reaction zone was maintained at 331° C. At this temperature, the conversion based on cyclohexanol used was 70%. The reaction mixture leaving the reactor was cooled to room temperature with release of hydrogen. The liquid reaction products were analyzed by gas chromatography. At a conversion of 70%, a selectivity of 99.0% and a residue of 0.70% were obtained after 1800 hours. The catalyst ($C1_{1800}$) had the physical properties shown in Table 1.

Comparative Example 1

Preparation of an Uncalcined Catalyst and Dehydrogenation Therewith

Calcium carbonate and zinc hydroxide carbonate were precipitated from an aqueous zinc and calcium nitrate solution by means of 2M sodium carbonate solution, as described in Example 1. The precipitate was washed free of nitrate and after slurrying with $H_2O$ was spray dried. The dry powder thus obtained was, after addition of 2% by weight of graphite, pressed to give 5×5 mm pellets. The catalyst thus obtained ("$C2_0$") has the physical properties indicated in Table 1. X-ray analysis shows calcite as main component and aragonite and zinc hydroxide carbonate as secondary components. 920 g of this catalyst were, as described in Example 2, tested at a cyclohexanol conversion of 70%. After 1800 hours, the selectivity of the catalyst was 98.5% and the amount of residue formed was 0.88%. The catalyst ($C2_{1800}$) had the physical properties indicated in Table 1.

Example 3

Dehydrogenation Using $C1_0$ (140 h)

920 g of the catalyst ($C1_0$) prepared as described in Example 1 were installed in a tube reactor having a length of 0.6 m and an internal diameter of 0.05 m. Via a vaporizer, 640 ml/h of liquid cyclohexanol were fed in gaseous form into the reactor. 7 l/h of hydrogen were metered in upstream of the reactor. The temperature in the reaction zone was maintained at 341° C. At this temperature, the conversion based on cyclohexanol used was 70%. The reaction mixture leaving the reactor was cooled to room temperature with release of hydrogen. The liquid reaction products were analyzed by gas chromatography. At a conversion of 70%, a selectivity of 98.7% and a residue of 0.80% were obtained after 140 hours. The catalyst was removed from the reactor ($C1_{140}$) and had the physical properties indicated in Table 1.

Comparative Example 2

Dehydrogenation Using $C2_0$, Without Hydrogen

Example 3 was repeated using catalyst ($C2_0$) from Comparative Example 1 with the further differences that no hydrogen was used, the reaction temperature was 323° C. and the duration of the experiment was 143 hours. At a conversion of 70%, the selectivity based on cyclohexanol used was 96.6% and the residue was 2.37%. The catalyst removed from the reactor ($C2_{143}$) had the physical properties indicated in Table 1.

TABLE 1

Physical data for the catalysts

| Example No. | BET surface area [$m^2$/g] | Total pore volume in the range from 0.005 to 300 µm pore diameter [$m^3$/g] | Pore volume in the pore diameter range from 0.01 to 0.5 µm [%] | Compressive strength on the end face N/$cm^2$ | Lateral compressive strength [N] | Phases by X-ray analysis | Operating time [h] |
| --- | --- | --- | --- | --- | --- | --- | --- |
| 1($C1_0$) | 14.6 | 0.23 | 96.8 | 1947 | 94 | $CaCO_3$ calcite (main component) <br> ZnO (secondary component) <br> C graphite | 0 |
| 2($C1_{1800}$) | 12.1 | 0.21 | 94.5 | 847 | 46 | $CaCO_3$ calcite (main component) <br> $CaCO_3$ aragonite (secondary component) <br> $Zn_4CO_3(OH)_6 \cdot H_2O$ <br> C graphite | 1800 |
| Comparative Example 1 ($C2_0$) | 12.5 | 0.19 | 84.0 | 1807 | 70 | $CaCO_3$ calcite (main component) <br> $CaCO_3$ aragonite (secondary component) <br> $Zn_4CO_3(OH)_6 \cdot H_2O$ <br> C graphite | 0 |
| Comparative Example 1 ($C2_{1800}$) | 17.3 | 0.27 | 72.5 | 664 | 18 | $CaCO_3$ calcite (main component) <br> ZnO (secondary component) <br> $CaCO_3$ aragonite (small amount) C graphite | 1800 |

The catalyst $C1_0$ according to the present invention has both a higher compressive strength on the end face and a higher lateral compressive strength than the uncalcined catalyst $C2_0$. Furthermore the lateral compressive strength of the catalyst C1 only drops after 1800 hours to 49% of the initial value of the lateral compressive strength, while in the case of comparative catalyst $C2_{1800}$ containing aragonite the lateral compressive strength drops to a quarter (26%) of the initial value, which in industrial use means more down time for replacing the aragonite-containing catalyst.

TABLE 2

Overview of the dehydrogenation experiments

| Example | Temperature [° C.] | Selectivity [%] | Amount of hydrogen added [l/h] | Conversion [%] | Residue[1] [%] | Catalyst |
|---|---|---|---|---|---|---|
| 2 | 331 | 99.0 | 7 | 70 | 0.70 | $C1_0\text{-->}C1_{1800}$ |
| Comparative Example 1 | 331 | 98.5 | 7 | 70 | 0.88 | $C2_0\text{-->}C2_{1800}$ |
| 3 | 341 | 98.7 | 7 | 70 | 0.80 | $C1_0\text{-->}C1_{140}$ |
| Comparative Example 2 | 323 | 96.6 | 0 | 70 | 2.37 | $C2_0\text{-->}C2_{143}$ |

[1]Residue: based on the total mass of the liquid reaction mixture

We claim:

1. A dehydrogenation catalyst having active components comprising from 30 to 60% by weight of zinc oxide and from 40 to 70% by weight of calcium carbonate, wherein, prior to the catalyst's utilization in a dehydrogenation reaction, only calcite and zinc oxide can be detected by X-ray diffractometry, and which catalyst, in a pellet form, has a compressive strength on the end face in the range of from 500 to 4000 N/cm$^2$ and a lateral compressive strength in the range of from 30 to 300 N.

2. The dehydrogenation catalyst defined in claim 1 having a pore volume at a pore diameter in the range from 5 nm to 300 µm of from 0.1 to 0.5 cm$^3$/g.

3. The dehydrogenation catalyst defined in claim 1, wherein at least 85% of the pore volume of the catalyst has a pore diameter in the range from 0.01 to 0.5 µm.

4. A process for preparing the dehydrogenation catalyst defined in claim 1 by precipitation of sparingly soluble zinc and calcium compounds from water-soluble zinc and calcium salt solutions using a base and subsequent work-up, comprising (a) using a water-soluble basic carbonate as the base, (b) optionally filtering off the sparingly soluble zinc and calcium compounds after precipitation, (c) washing the precipitated zinc and calcium compounds, or the zinc and calcium compounds which have been filtered off, (d) drying the washed zinc and calcium compounds from (c) to give a dried precursor, and subsequently (e) calcining the dried precursor from (d) at a temperature of from 400 to not above 600° C. in the presence of air, and (f) optionally pressing the calcined product to give shaped bodies.

5. The process defined in claim 4, wherein after step (c) and before step (d) the washed zinc and calcium compounds are pressed to give shaped bodies.

6. The process defined in claim 4, wherein the precipitate of sparingly soluble zinc and calcium compounds is washed on filter presses, the resulting filter cake is subsequently slurried with water, the slurry is then dried by spraying in a spray drier and the powder obtained is then further processed as described under (e) and optionally (f).

7. A process for the dehydrogenation of a secondary cyclic alcohol, which comprises providing the catalyst defined in claim 1, and dehydrogenating said alcohol with the catalyst at a temperature of from 200 to 500° C. in the gas phase in the presence of hydrogen.

8. The process defined in claim 7, wherein the secondary cyclic alcohol is cyclohexanol.

9. The process defined in claim 7, wherein the catalyst has a BET specific surface area in the range from 5 to 50 m$^2$/g.

10. The process defined in claim 7, wherein the catalyst has a pore volume at a pore diameter in the range from 5 nm to 300 µm of from 0.1 to 0.5 cm$^3$/g.

11. The process defined in claim 10, wherein at least 85% of the pore volume has a pore diameter in the range from 0.01 to 0.5 µm.

* * * * *